(12) United States Patent
Lewis et al.

(10) Patent No.: US 8,053,520 B2
(45) Date of Patent: Nov. 8, 2011

(54) CONJUGATION REACTIONS

(75) Inventors: Andrew Lennard Lewis, Surrey (GB); Simon William Leppard, Surrey (GB)

(73) Assignee: Biocompatibles UK Limited, Farnham (GB)

( * ) Notice: Subject to any disclaimer, the term of this patent is extended or adjusted under 35 U.S.C. 154(b) by 977 days.

(21) Appl. No.: 10/542,333

(22) PCT Filed: Jan. 16, 2004

(86) PCT No.: PCT/GB2004/000140
§ 371 (c)(1),
(2), (4) Date: Jul. 13, 2005

(87) PCT Pub. No.: WO2004/063237
PCT Pub. Date: Jul. 29, 2004

(65) Prior Publication Data
US 2006/0135714 A1 Jun. 22, 2006

(30) Foreign Application Priority Data
Jan. 16, 2003 (GB) .................................. 0301014.7

(51) Int. Cl.
A61K 47/48 (2006.01)
C08G 63/48 (2006.01)
C08G 63/91 (2006.01)
C08L 89/00 (2006.01)

(52) U.S. Cl. ................................................... 525/54.1

(58) Field of Classification Search .................. 525/54.1
See application file for complete search history.

(56) References Cited

U.S. PATENT DOCUMENTS

| | | | | |
|---|---|---|---|---|
| 5,122,614 A * | 6/1992 | Zalipsky | ....................... | 548/520 |
| 5,191,015 A * | 3/1993 | Sheppard et al. | ............ | 525/54.1 |
| 5,198,493 A * | 3/1993 | Holmberg et al. | ........... | 525/54.1 |
| 5,260,373 A * | 11/1993 | Profy et al. | .................. | 525/54.1 |
| 5,328,955 A * | 7/1994 | Rhee et al. | .................... | 525/54.1 |
| 5,444,150 A * | 8/1995 | Inman et al. | .................. | 530/300 |
| 5,658,561 A * | 8/1997 | Nakabayashi et al. | ..... | 424/78.37 |
| 5,807,937 A * | 9/1998 | Matyjaszewski et al. | .... | 526/135 |
| 5,855,987 A * | 1/1999 | Margel et al. | ............... | 428/195.1 |
| 5,888,990 A | 3/1999 | Chasalow | | |
| 5,932,462 A * | 8/1999 | Harris et al. | .................. | 435/188 |
| 6,113,906 A * | 9/2000 | Greenwald et al. | ........ | 424/194.1 |
| 6,127,349 A * | 10/2000 | Chasalow | ....................... | 514/77 |
| 6,251,382 B1 * | 6/2001 | Greenwald et al. | ........ | 424/78.17 |
| 6,310,149 B1 | 10/2001 | Haddleton | | |
| 6,562,330 B1 | 5/2003 | Stratford et al. | | |
| 6,803,438 B1 * | 10/2004 | Brocchini et al. | ......... | 526/292.1 |
| 6,828,029 B1 * | 12/2004 | Lewis et al. | .................. | 428/446 |
| 6,833,276 B2 * | 12/2004 | Klaerner et al. | ............. | 436/532 |
| 6,852,816 B2 | 2/2005 | Lewis et al. | | |
| 7,300,990 B2 | 11/2007 | Lewis et al. | | |
| 7,365,127 B2 * | 4/2008 | Wu et al. | ....................... | 525/118 |
| 2002/0141965 A1 * | 10/2002 | Ahn et al. | .................. | 424/78.17 |
| 2003/0158333 A1 * | 8/2003 | Roberts et al. | ............. | 525/54.11 |
| 2004/0029794 A1 * | 2/2004 | Veronese et al. | ................ | 514/12 |
| 2004/0030101 A1 * | 2/2004 | Bailon et al. | .................. | 530/351 |
| 2004/0091451 A1 * | 5/2004 | Charreyre et al. | .......... | 424/78.19 |
| 2004/0157276 A1 * | 8/2004 | Sumida et al. | ............... | 435/7.23 |
| 2004/0162388 A1 * | 8/2004 | Tjoeng | .......................... | 525/54.1 |
| 2004/0235734 A1 * | 11/2004 | Bossard et al. | ................. | 514/12 |
| 2005/0112203 A1 * | 5/2005 | Shau et al. | .................... | 424/486 |
| 2005/0123501 A1 | 6/2005 | Lewis | | |
| 2005/0163743 A1 | 7/2005 | Lewis | | |
| 2005/0220880 A1 | 10/2005 | Lewis | | |
| 2006/0069203 A1 | 3/2006 | Lewis | | |
| 2007/0123646 A1 * | 5/2007 | Lele et al. | ..................... | 525/54.1 |
| 2007/0276088 A1 * | 11/2007 | Maynard et al. | ............. | 525/54.1 |
| 2008/0206182 A1 * | 8/2008 | Sommermeyer et al. | .. | 424/78.17 |
| 2010/0166700 A1 | 7/2010 | Charles | | |

FOREIGN PATENT DOCUMENTS

| | | |
|---|---|---|
| JP | 2000093169 A * | 4/2000 |
| WO | WO 93/01221 A1 | 1/1993 |
| WO | 93/15775 A1 | 8/1993 |
| WO | WO 96/30421 A1 | 10/1996 |
| WO | 98/43676 A1 | 10/1998 |
| WO | 01/27209 A1 | 4/2001 |
| WO | WO 02/28929 A1 | 4/2002 |
| WO | WO 02/100439 A | 12/2002 |
| WO | WO 03/062290 A1 | 7/2003 |
| WO | WO 03/074026 A1 | 9/2003 |
| WO | WO 03/074090 A2 | 9/2003 |
| WO | WO 03/074090 A3 | 9/2003 |

OTHER PUBLICATIONS

Monfardini et al. (Bioconjuate Chem. 1995, 6, 62-69).*
Chen et al. J. Biomater. Sci. Polymer Edn. vol. 5(4), p. 371-382, 1994.*
Machine Translation of JP 2000-093169 A, 2010.*
E.J. Ashford et al., "First example of the atom transfer radical polymerization of an acidic monomer: direct synthesis of methacrylic acid copolymers in aqueous media", Chem. Commun.,, XP-002276944, 1999, pp. 1285-1286.
Chen et al, "Controlled/'living' radical polymerization of MMA via in situ ATRP process", Chem. Commun., 2000, pp. 233-234.

* cited by examiner

Primary Examiner — Mark Eashoo
Assistant Examiner — Liam Heincer
(74) Attorney, Agent, or Firm — Sughrue Mion, PLLC

(57) ABSTRACT

An initiator for the terminal group of the polymer product of an atom or group radical transfer polymerisation has an activated carboxyl or an amine group which is reacted with an amine or carboxyl (respectively) group containing biologically active compound. The initiator is preferably 4-(3-(2-bromo, 2-methyl-propionate)phenyl)-propionic acid N-hydroxysuccinimide ester or 2-bromo, 2-methyl-propionic acid N-hydroxysuccinimide ester. The monomers preferably comprise a zwitterionic monomer such as 2-methacryloxyethyl-2'-trimethyl ammoniumethyl phosphate inner salt.

6 Claims, No Drawings

CONJUGATION REACTIONS

The present invention relates to forming conjugates of polymers and biologically active compounds, and to functional polymer precursors therefore.

We have described in WO-A-2003062290 (unpublished at the priority date hereof) the concept of taking a biologically active drug molecule and reacting it with a compound so as to functionalise it with an appropriate brominated moiety. The modified drug is capable of initiating an atom transfer radical polymerisation (ATRP) with monomers such as 2-methacryloyloxyethyl-2'-trimethylammonium ethyl phosphate inner salt. The compound 2-bromo-2-methyl propionic acid bromide is one such bromine-functionalising agent, the acid bromide portion reacting with any active hydroxyl group on the drug compound to produce a brominated analogue of a methacrylate moiety that has been shown to be eminently suitable for initiating ATRP (see works of Matyjaszewski, Armes and Haddleton). With this functionalising agent, this reaction is only possible in cases where the drug molecule and the 2-bromo, 2-methyl propionic acid bromide are both soluble in some organic solvent that is not reactive towards the acid bromide. In that specification we also describe a bromine-functionalising agent which is used to acylate an amine group, namely of a protein. The subject matter has a common priority date as claims of the present case and of example 4 herein.

It may be desirable to functionalise large biological entities such as proteins and antibodies with polymers. Roche and Schering-Plough both have on the market successful interferon-based products that have been modified by PEGylation of the biological entity. The attachment of polyethylene glycol chains to interferon has improved its plasma half-life (i.e. reduced the rate at which the body removes the antibody from the bloodstream), essentially by reduced renal clearance and lowering opsonisation (protein binding). It is of interest to modify such biological entities with other polymers, particularly those based on phosphorylcholine because of their enhanced haemocompatibility.

In U.S. Pat. No. 6,310,149 ATRP processes are described in which the initiator comprises a functional group which is a derivative of an organic acid. The acid may be a carboxylic acid or alternatively a phosphorus based acid or sulphonic acid. Examples of initiators are esters of various acids. Monomers which are polymerised include methylmethacrylate, styrene, benzylmethacrylate and 2-hydroxyethylmethacrylate. The polymerisations appear to be solvent-free, that is liquid monomer is the liquid medium for the polymerisation reaction.

Wang, J-S, et al in Polym. Mater. Sci. Eng. 73 (1995) 416 to 417 describe the use of bis-functional initiators for ATRP, whereby the residual group derived from the initiator may be used in subsequent reactions. Examples of end groups or precursors thereof are carboxyl groups, hydroxyl groups and cyano groups.

The present invention relates to a new process for forming a biologically active conjugate compound comprising a conjugation step in which a biologically active starting material of the general formula I

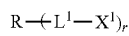   I is reacted in an amide bond forming step with a reagent of the general formula II

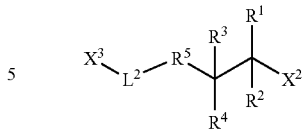

to form an amide-linked conjugate,
in which R is a biologically active moiety;
$L^1$ is a bond or a divalent organic linker; and
$X^1$ is —$NHR^6$ or —$COR^7$, in which $R^6$ is hydrogen, $C_{1-6}$ alkyl, aryl or an amine activating group and $R^7$ is hydroxyl or a carboxyl activating group;

$X^2$ is selected from the group consisting of a polymer formed from ethylenically unsaturated monomers and joined through a terminal group, Cl, Br, I, $OR^{10}$, $SR^{14}$, $SeR^{14}$, $OP(=O)R^{14}$, $OP(=O)(OR^{14})_2$, O—$N(R^{14})_2$ and S—$C(=S)N(R^{14})_2$, where $R^{10}$ is alkyl of from 1 to 20 carbon atoms in which each of the hydrogen atoms may be independently replaced by halide, $R^{14}$ is aryl or a straight or branched $C_1$-$C_{20}$ alkyl group, and where an $N(R^{14})_2$ group is present, the two $R^{14}$ groups may be joined to form a 5- or 6-membered heterocyclic ring;

$R^1$ and $R^2$ are each independently selected from the group consisting of H, halogen, $C_1$-$C_{20}$ alkyl, $C_3$-$C_8$ cycloalkyl, $C(=O)R^{15}$, $C(=O)NR^{16}R^{17}$, COCl, OH, CN, $C_2$-$C_{20}$ alkenyl, oxiranyl, glycidyl, aryl, heterocyclyl, aralkyl and aralkenyl, in any of which the alkyl, alkenyl or aryl, heterocyclyl or cycloalkyl groups there may be from 1 to 3 substituents selected from the group consisting of hydrogen, hydroxy $C_1$-$C_4$ alkoxy, acyloxy, aryl, heterocyclyl, $C(=O)R^{15}$, $C(=O)NR^{16}R^{17}$, oxyranyl and glycidyl; $R^{15}$ is alkyl of from 1 to 20 carbon atoms, alkoxy of from 1 to 20 carbon atoms, oligo(alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, acyloxy, alkoxy, alkoxycarbonyl, alkenoxycarbonyl, aryl and hydroxy), and hydroxyl groups;

$R^{16}$ and $R^{17}$ are independently H or alkyl of from 1 to 20 carbon atoms which alkyl groups, in turn may have substituents selected from alkoxy, acyl, acyloxy, alkoxycarbonyl, alkenoxycarbonyl, aryl and hydroxy, or $R^{16}$ and $R^{17}$ may be joined together to form an alkanediyl group of from 2 to 5 carbon atoms, thus forming a 3- to 6-membered ring.

$R^3$ and $R^4$ are independently selected from hydrogen, and $C_{1-6}$ alkyl or $R^3$ and $R^4$ together are =O or =$NR^8$ where $R^8$ is hydrogen or $C_{1-4}$ alkyl;

$R^5$ is a bond, —O—, —S— or a divalent organic group;
$L^2$ is a bond or a divalent linker and,
where $X^1$ is $NHR^6$, $X^3$ is $COR^7$ and
where $X^1$ is $COR^7$, $X^3$ is $NHR^6$ and
r is an integer of at least 1.

In the conjugation reaction an amide bond is formed from the reaction of the carboxyl functionality $COR^7$ and the amine functionality —$NHR^6$, of $X^1$ and $X^3$. Known activating agents may be used to assist the formation of the amide bond, such as carbodiimides and/or N-hydroxysuccinimide. Preferably $R^7$ is an N-succinimidyloxy group. $R^6$ may be a $C_{1-6}$ alkyl or aryl group, but is preferably hydrogen.

Preferably the conjugation reacting step is carried out in a protic solvent e.g. a lower alkanol and/or, most preferably, water.

Where $X^2$ is other than a polymer chain, the amide conjugate product may be used as an initiator for an atom- or group transfer radical polymerisation reaction.

The ethylenically unsaturated monomers used in such a polymerisation may be any which may be codissolved with the amide in a suitable solvent for such a polymerisation, such as an organic or aqueous solvent. The invention is of most utility for polymerising hydrophilic monomers, that is which are soluble in water, lower alkanols ($C_{1-4}$-alkanols, including glycols) or glycol ethers. The polymerisation is generally conducted in the presence of one of these solvents, in which the monomers are dissolved. Conveniently the solvent includes water.

Suitable monomers have the general formula III

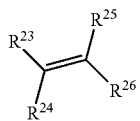

III in which $R^{23}$ is selected from the group consisting of hydrogen, halogen, $C_{1-4}$ alkyl and groups $COOR^{27}$ in which $R^{27}$ is hydrogen and $C_{1-4}$ alkyl;

$R^{24}$ is selected from the group consisting of hydrogen, halogen and $C_{1-4}$ alkyl;

$R^{25}$ is selected from the group consisting of hydrogen, halogen, $C_{1-4}$ alkyl and groups $COOR^{27}$ provided that $R^{23}$ and $R^{25}$ are not both $COOR^{27}$; and $R^{26}$ is selected from the group consisting of $C_{1-10}$ alkyl, $C_{1-20}$ alkoxycarbonyl, mono- and di-($C_{1-20}$ alkyl) amino carbonyl, $C_{6-20}$ aryl (including alkaryl), $C_{7-20}$ aralkyl, $C_{6-20}$ aryloxycarbonyl, $C_{7-20}$-aralkyloxycarbonyl, $C_{6-20}$ arylamino carbonyl, $C_{7-20}$ aralkyl-amino carbonyl, hydroxyl and carboxylic $C_{2-10}$ acyloxy groups, any of which may have one or more substituents selected from the group consisting of halogen atoms, alkoxy, oligo-alkoxy, aryloxy, acyloxy, acylamino, amine (including mono and di-alkyl amino and tri-alkylammonium in which the alkyl groups may be substituted), carboxyl, sulphonyl, phosphoryl, phosphino, (including mono- and di-alkyl phosphine and tri-alkylphosphonium), zwitterionic, hydroxyl, vinyloxycarbonyl and other vinylic and allylic groups, and reactive silyl and sily-loxy groups, such as trialkoxysilyl groups;

or $R^{26}$ and $R^{25}$ or $R^{25}$ and $R^{23}$ may together form $-CONR^{28}CO$ in which $R^{28}$ is a $C_{1-20}$ alkyl group.

It is preferred for at least two of the groups $R^{23}$, $R^{24}$, $R^{25}$ and $R^{26}$ to be halogen or, more preferably, hydrogen atoms. Preferably $R^{23}$ and $R^{24}$ are both hydrogen atoms. It is particularly preferred that compound of general formula III be a styrene-based or (alk) acrylic based compound. In styrene based compounds $R^{26}$ represents an aryl group, especially a substituted aryl group in which the substituent is an amino alkyl group, a carboxylate or a sulphonate group. Where the comonomer is an (alk) acrylic type compound, $R^{26}$ is an alkoxycarbonyl, an alkyl amino carbonyl, or an aryloxy carbonyl group $R^{23}$ and $R^{24}$ are each hydrogen and $R^{25}$ is hydrogen or $C_{1-4}$ alkyl. Most preferably in such compounds $R^{26}$ is a $C_{1-20}$-alkoxy carbonyl group, optionally having a hydroxy substituent. (Alk) acrylic compounds are generally methacrylic in which case $R^{25}$ is methyl.

Preferably the monomers include a zwitterionic monomer having the general formula IV

IV in which Y is an ethylenically unsaturated group selected from $H_2C=CR^{17}-CO-A-$, $H_2C=CR^{17}-C_6H_4-A^1-$, $H_2C=CR^{17}-CH_2A^{18}$, $R^2O-CO-CR^{17}=CR^{17}-CO-O$, $R^{17}CH=CH-CO-O-$, $R^{17}CH=C(COOR^{18})CH_2-CO-O$,

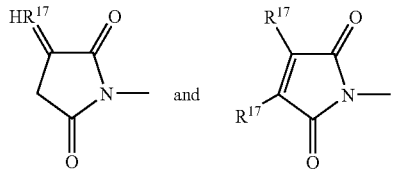

A is $-O-$ or $NR^{19}$;
$A^1$ is selected from a bond, $(CH_2)_lA^2$ and $(CH_2)_lSO_3-$ in which l is 1 to 12;
$A^2$ is selected from a bond, $-O-$, $O-CO-$, $CO-O$, $CO-NR^1-$, $-NR^1-CO$, $O-CO-NR^1-$, $NR^1-CO-O-$;
$R^{17}$ is hydrogen or $C_{1-4}$ alkyl;
$R^{19}$ is hydrogen, $C_{1-4}$ alkyl or BX;
$R^{18}$ is hydrogen or $C_{1-4}$ alkyl;
B is a bond, or a straight branched alkanediyl, alkylene oxaalkylene, or alkylene (oligooxalkylene) group, optionally containing one or more fluorine substituents; and
X is a zwitterionic group.

Preferably X is an ammonium, phosphonium, or sulphonium phosphate or phosphonate ester zwitterionic group, more preferably a group of the general formula V

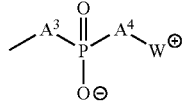

V in which the moieties $A^3$ and $A^4$, which are the same or different, are $-O-$, $-S-$, $-NH-$ or a valence bond, preferably $-O-$, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula $-W^1-N^+R^{20}_3$, $-W^1-P^+R^{21}_3$, $-W^1-S^+R^{21}_2$ or $-W^1-Het^+$ in which:

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^{20}$ are the same or different and each is hydrogen or alkyl of 1 to 4 carbon atoms, preferably methyl, or aryl, such as phenyl, or two of the groups $R^{20}$ together with the nitrogen atom to which they are attached form an aliphatic heterocyclic ring containing from 5 to 7 atoms, or the three groups $R^{20}$ together with the nitrogen atom to which they are attached as heteroaromatic ring having 5 to 7 atoms, either of which rings may be fused with another saturated or unsaturated ring to form a fused ring structure containing from 5 to 7 atoms in each ring, and optionally one or more of the groups $R^{20}$ is substituted by a hydrophilic functional group, and the groups $R^{21}$ are the same or different and each is $R^{20}$ or a group $OR^{20}$, where $R^{20}$ is as defined above; or Het is an aromatic nitrogen-, phosphorus- or sulphur-, preferably nitrogen-, containing ring, for example pyridine.

Monomers in which X is of the general formula in which $W^+$ is $W^1N^TR^{20}{}_3$ may be made as described in our earlier specification WO-A-9301221. Phosphonium and sulphonium analogues are described in WO-A-9520407 and WO-A-9416749.

Generally a group of the formula V has the preferred general formula VI

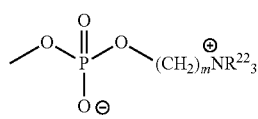

VI where the groups $R^{22}$ are the same or different and each is hydrogen or $C_{1-4}$ alkyl, and m is from 1 to 4, in which preferably the groups $R^{22}$ are the same preferably methyl.

In phosphobetaine based groups, X may have the general formula VII

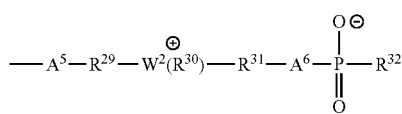

VII in which $A^5$ is a valence bond, —O—, —S— or —NH—, preferably —O—;

$R^9$ is a valence bond (together with $A^5$) or alkanediyl, —C(O)alkylene- or —C(O)NH alkylene preferably alkanediyl, and preferably containing from 1 to 6 carbon atoms in the alkanediyl chain;

$W^2$ is S, $PR^{30}$ or $NR^{30}$;

the or each group $R^{30}$ is hydrogen or alkyl of 1 to 4 carbon atoms or the two groups $R^{30}$ together with the heteroatom to which they are attached form a heterocyclic ring of 5 to 7 atoms;

$R^{31}$ is alkanediyl of 1 to 20, preferably 1 to 10, more preferably 1 to 6 carbon atoms;

$A^6$ is a bond, NH, S or O, preferably O; and $R^{32}$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Monomers comprising a group of the general formula VII may be made by methods as described in JP-B-03-031718, in which an amino substituted monomer is reacted with a phospholane.

In compounds comprising a group of the general formula VII, it is preferred that $A^5$ is a bond;
$R^{29}$ is a $C_{2-6}$ alkanediyl;
$W^2$ is $NR^7$:
each $R^7$ is $C_{1-4}$ alkyl;
$R^{31}$ is $C_{2-6}$ alkanediyl;
$A^6$ is O; and
$R^{32}$ is $C_{1-4}$ alkoxy.

Alternatively X may be a zwitterion in which the anion comprises a sulphate, sulphonate or carboxylate group.

One example of such a group is a sulphobetaine group, of the general formula VIII

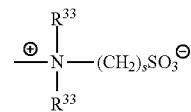

VIII where the groups $R^{33}$ are the same or different and each is hydrogen or $C_{1-4}$ alkyl and s is from 2 to 4.

Preferably the groups $R^{33}$ are the same. It is also preferable that at least one of the groups $R^{33}$ is methyl, and more preferable that the groups $R^{33}$ are both methyl.

Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer. Such groups may be represented by the general formula IX

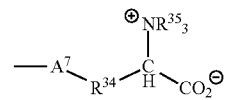

IX in which $A^7$ is a valence bond, —O—, —S— or —NH—, preferably —O—, $R^{34}$ is a valence bond (optionally together with $A^7$) or alkanediyl, —C(O)alkylene- or —C(O)NHalkylene, preferably alkanediyl and preferably containing from 1 to 6 carbon atoms; and the groups $R^{35}$ are the same or different and each is hydrogen or alkyl of 1 to 4 carbon atoms, preferably methyl, or two or three of the groups $R^{35}$, together with the nitrogen to which they are attached, form a heterocyclic ring of from 5 to 7 atoms, or the three group $R^{35}$ together with the nitrogen atom to which they are attached form a fused ring heterocyclic structure containing from 5 to 7 atoms in each ring.

Another example of a zwitterion having a carboxylate group is a carboxy betaine —$N^\Gamma(R^{36})_2(CH_2)_u COO^\Gamma$ in which the $R^{36}$ groups are the same or different and each is hydrogen or $C_{1-4}$ alkyl and u is 2 to 6, preferably 2 or 3.

In the zwitterionic monomer of the general formula IV it is preferred that the ethylenic unsaturated group Y is $H_2C=CR^{17}$—CO-A-. Such (alk) acrylic moieties are preferably methacrylic, that is in which $R^{17}$ is methyl, or acrylic, in which $R^{17}$ is hydrogen. Whilst the compounds may be (alk) acrylamido compounds, that is in which A is $NR^{19}$, in which case $R^{19}$ is preferably hydrogen, or less preferably, methyl, most preferably the compounds are esters, that is in which A is O.

In monomers of the general formula IV, especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-2'-trimethylammonium ethyl phosphate inner salt (MPC).

Another suitable monomer is a compound which is a mono-, di-, or oligo-hydroxy $C_{2-6}$ alkyl(alk)acrylate or -(alk)acrylamide, an oligo (ethoxy) alkyl(alk)acrylate or acrylamide or a N,N-dimethyl(alk)acrylamide.

Where $X^2$ is a polymer chain the reagent of the general formula II may be made in a preliminary polymerisation step in which ethylenically unsaturated monomers are polymerised in the presence of an initiator of the general formula XI

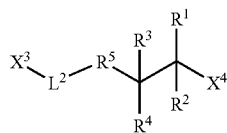
XI in which $X^3$, $L^2$ and $R^1$ to $R^5$ are as defined in relation to general formula II and $X^4$ is selected from the group consisting of Cl, Br, I, $OR^{51}$, $SR^{52}$, $SeR^{52}$, $OP(=O)R^{52}$, $OP(=O)(OR^{52})_2$, O—N$(R^{52})_2$ and S—C(=S)N$(R^{52})_2$, where $R^{51}$ is alkyl of from 1 to 20 carbon atoms in which each of the hydrogen atoms may be independently replaced by halide, $R^{52}$ is aryl or a straight or branched $C_1$-$C_{20}$ alkyl group, and where an N$(R^{52})_2$ group is present, the two $R^{52}$ groups may be joined to form a 5- or 6-membered heterocyclic ring.

In this atom or group transfer radical polymerisation process the ethylenically unsaturated monomers which are polymerised may be of the same type as are described above in relation to polymerisation processes in which the amide conjugate is used as the initiator.

A group or atom transfer radical polymerisation is carried out in the presence of a catalyst, which comprises a transition metal salt and a ligand. The transition metal compound which comprises a component of the catalyst is $M_q^{n+}X^5_q$, where:

$M_t^{q+}$ may be selected from the group consisting of $Cu^{1+}$, $Cu^{2+}$, $Fe^{2+}$, $Fe^{3+}$, $Ru^{2+}$, $Ru^{3+}$, $Cr^{2+}$, $Cr^{3+}$, $Mo^{2+}$, $Mo^{3+}$, $W^{2+}$, $W^{3+}$, $Mn^{2+}$, $Mn^{3+}$, $Mn^{4+}$, $Rh^{3+}$, $Rh^{4+}$, $Re^{2+}$, $Re^{3+}$, $Co^+$, $Co^{2+}$, $Co^{3+}$, $V^{2+}$, $V^{3+}$, $Zn^+$, $Zn^{2+}$, $Ni^{2+}$, $Ni^{3+}$, $Au^+$, $Au^{2+}$, $Ag^+$ and $Ag^{2+}$;

$X^5$ is selected from the group consisting of halogen, $C_1$-$C_6$-alkoxy, $(SO_4)_{1/2}$, $(PO_4)_{1/3}$, $(R^{18}PO_4)\frac{1}{2}$ $(R^{18}_2PO_4)$, triflate, hexafluorophosphate, methanesulphonate, arylsulphonate, CN and $R^{19}CO_2$, where $R^{18}$ is aryl or a straight or branched $C_{1-20}$ alkyl and $R^{19}$ is H or a straight or branched $C_1$-$C_6$ alkyl group which may be substituted from 1 to 5 times with a halogen; and q is the formal charge on the metal ($0 \leq n \leq 7$).

Preferably $X^5$ is halide, most preferably chloride or bromide. Particularly suitable transition metal compounds are based on copper or ruthenium, for instance CuCl or $RuCl_2$.

In the catalyst, the ligand is preferably selected from the group consisting of:

a) compounds of the formulas:

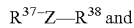

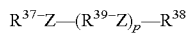

where:

$R^{37}$ and $R^{38}$ are independently selected from the group consisting of H, $C_1$-$C_{20}$ alkyl, aryl, heterocyclyl and $C_1$-$C_6$ alkoxy, $C_1$-$C_4$ dialkylamino, $C(=O)R^{40}$, $C(=O)R^{41}R^{42}$ and $A^8C(=O)R^{43}$, where $A^8$ may be $NR^{44}$ or O; $R^{40}$ is alkyl of from 1 to 20 carbon atoms, aryloxy or heterocyclyloxy; $R^{41}$ and $R^{42}$ are independently H or alkyl of from 1 to 20 carbon atoms or $R^{41}$ and $R^{42}$ may be joined together to form an alkanediyl group of from 2 to 5 carbon atoms, thus forming a 3- to 6-membered ring; $R^{43}$ is H, straight or branched $C_1$-$C_{20}$ alkyl or aryl and $R^{44}$ is hydrogen, straight or branched $C_{1-20}$-alkyl or aryl; or $R^{37}$ and $R^{38}$ may be joined to form, together with Z, a saturated or unsaturated ring;

Z is O, S, $NR^{45}$ or $PR^{46}$, where $R^{46}$ is selected from the same group as $R^{37}$ and $R^{38}$, and where Z is $PR^{46}$, $R^{46}$ can also $C_1$-$C_{20}$ alkoxy or Z may be a bond, $CH_2$ or a fused ring, where one or both of $R^{37}$ and $R^{38}$ is heterocyclyl, each $R^{39}$ is independently a divalent group selected from the group consisting of $C_1$-$C_8$ cycloalkanediyl, $C_1$-$C_8$ cycloalkanediyl, arenediyl and heterocyclylene where the covalent bonds to each Z are at vicinal positions or $R^{39}$ may be joined to one or both of $R^{37}$ and $R^{38}$ to formulate a heterocyclic ring system; and p is from 1 to 6;

b) CO;

c) porphyrins and porphycenes, which may be substituted with from 1 to 6 halogen atoms, $C_{1-6}$ alkyl groups, $C_{1-6}$-alkoxy groups, $C_{1-6}$ alkoxycarbonyl, aryl groups, heterocyclyl groups, and $C_{1-6}$alkyl groups further substituted with from 1 to 3 halogens;

d) compounds of the formula $R^{47}R^{48}C(C(=O)R^{49})_2$, where $R^{49}$ is $C_{1-20}$alkyl, $C_{1-20}$ alkoxy, aryloxy or heterocyclyloxy; and each of $R^{47}$ and $R^{48}$ is independently selected from the group consisting of H, halogen, $C_{1-20}$ alkyl, aryl and heterocyclyl, and $R^{47}$ and $R^{48}$ may be joined to form a $C_{1-8}$ cycloalkyl ring or a hydrogenated aromatic or heterocyclic ring, of which the ring atoms may be further substituted with 1 to 5 $C_{1-6}$alkyl groups, $C_{1-6}$alkoxy groups, halogen atoms, aryl groups, or combinations thereof; and e) arenes and cyclopentadienyl ligands, where said cyclopentadienyl ligand may be substituted with from one to five methyl groups, or may be linked through and ethylene or propylene chain to a second cyclopentadienyl ligand.

Selection of a suitable ligand is, for instance, based upon the solubility characteristics and/or the separability of the catalyst from the product polymer mixture. Generally the catalyst is soluble in the liquid reaction mixture, although under some circumstances it may be possible to immobilise the catalyst, for instance on a porous substrate. For the preferred process, which is carried out in the liquid phase, the ligand is soluble in a liquid phase. The ligand is generally a nitrogen containing ligand. The preferred ligand may be a compound including a pyridyl group and an imino moiety, such as bipyridine, or

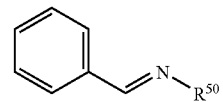

where $R^{50}$ is a suitable alkyl group, the substituent being variable and adaptable to confer desired solubility characteristics or may be triphenylphosphine or 1,1,4,7,10,10-hexamethyl-triethylene tetramine.

Such nitrogen-containing ligands are usefully used in combination with copper (I) chloride, copper (I) bromide or ruthenium chloride transition metal compounds as part of the catalyst.

The atom or group transfer radical polymerisation process of the invention is preferably carried out to achieve a degree of polymerisation in the range 2 to 100. Preferably the degree of polymerisation is in the range 5 to 50, more preferably in the range 10 to 25. In the preferred group or atom transfer radical polymerisation technique, the degree of polymerisation is directly related to the initial ratios of initiator to monomer. Preferably the ratio is in the range 1:(2 to 100), more preferably in the range of 1:(5 to 50), most preferably in the range 1:(10 to 25).

The ratio of metal compound and ligand in the catalyst should be approximately stoichiometric, based on the ratios of the components when the metal ion is fully complexed. The ratio should preferably be in the range 1:(0.5 to 2) more preferably in the range 1:(0.8 to 1.25). Preferably the range is about 1:1.

In the process, the catalyst may be used in amounts such that a molar equivalent quantity as compared to the level of initiator is present. However, since catalyst is not consumed in the reaction, it is generally not essential to include levels of catalyst as high as of initiator. The ratio of catalyst (based on transition metal compound) to initiator is preferably in the range 1:(1 to 50), more preferably in the range 1:(1 to 10).

In the invention $R^5$ is, for instance, a group joined to the carbon atom to which $R^3$ and $R^4$ are joined through an oxygen atom, a group —$NR^8$— where $R^8$ is hydrogen or $C_{1-4}$ alkyl, a carboxyl (provided that $R^3$ and $R^4$ together are not =O) or a alkyl carbon atom or aryl carbon atom. It may additionally comprise an alkanediyl group, cycloalkane-diyl, an oligo(alkoxy) alkyl, arylene or alkarylene group. At the end joined to $L^2$ it may comprise —O—, —S—, —CO— or $NR^8$ or may be joined to $L^2$ through an aromatic or aliphatic carbon atom.

Linkers $L^1$ and/or $L^2$ may comprise, for instance, the residue of a bifunctional linking reagent such as an oligo peptide, a compound having two similar functionalities, such as isocyanates epoxides hydroxyl, thiols, amines, carboxyls, aldehydes, or two different functionalities selected from the same list. Preferably where $L^1$ and/or $L^2$ is other than a bond, it is the residue of a hetero-bifunctional linking reagent especially a reagent comprising one carboxylic functionality and an amide, hydroxy or phenol functionality.

The invention allows conjugation of an biologically active moiety R to a polymer or initiator precursor of a polymer, using well understood conjugation reactions, which may be carried out under relatively mild conditions and with high efficiency, to form conjugates having controllable solubility, bioavailability, stability or delivery and targeting characteristics. For instance protein actives may be rendered more stable by conjugation to hydrophilic polymers, especially polymers having pendant zwitterionic groups. The active may, for instance be an antibody or fragment thereof, a cytokine, such as an integer or, a peptide therapeutic, a hormone, an enzyme. The polymer conjugated moiety may be cleavable after delivery, for instance where it is conjugated at an active site, or may be substantially non-cleavable provided the activity of the biologically active compound is not deleteriously affected. The biologically active moiety may be linked to $L^1X^1$ through functional pendant groups or terminal groups. On peptides the pendant groups may be side chains on amino acyl residues, especially amine, hydroxyl thiol or carboxyl groups. Similarly, on such compounds the terminal groups are amino groups or carboxyl groups. Since r may be greater than 1, this indicates that more than one of the potentially reactive functional pendant or terminal groups may be provided with $L^1X^1$ groups for subsequent conjugation.

Preliminary steps of attaching linkers and groups $X^1$ to biologically active molecules, including methods for controlling the site of the attachment, by suitable protection and activation strategies, are known and may be used herein.

The present invention also provides a conjugate of the general formula XII

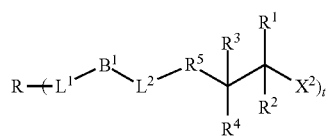

XII where $B^1$ is —$CONR^6$— or —$NR^6$—$CO$—
t is in the range 1 to r; and
R, $L^1$, $L^2$, $R^1$ to $R^5$ and $X^2$ are as defined above, as well as compositions comprising the compound and the compound for use in a method of treatment or diagnosis. The value of t may be an integer but need not be an integer as it will represent the average level of derivatisation across the population. Where t=r the biologically active molecule is fully derivatised.

The compound of formula XII, especially where it contains a linker $L^1$ or $L^2$, may be formed in an alternative sequence of steps in which the biologically active compound is conjugated to an intermediate reagent by a process other than amide bond formation. For instance the intermediate may be formed in a preliminary reaction in which the bond $B^1$ is formed. An example is described below in Example 4. The process of the first aspect of the invention is the preferred route for synthesising XII.

The invention also provides a polymerisation process in which ethylenically unsaturated monomers are polymerised by atom or group radical transfer polymerisation in the presence of an initiation selected from 4-(3-(2-bromo, 2-methyl-propionate)phenyl)-propionic acid N-hydroxysuccinimide ester and 2-bromo, 2-methyl-propionic acid N-hydroxysuccinimide ester. The monomers in the polymerisation are preferably as defined above in relation to the first aspect of the invention. The polymerisation is conducted in the same preferred solvents, preferably including water.

The compound 2-bromo, 2-methyl-propionic acid N-hydroxysuccinimide ester is believed to be a new compound and is thus claimed herein.

Polymer-biologically active compound conjugates may be useful pharmaceuticals eg as the compound may be a pro-drug. The conjugation may be used to control the solubility biological availability, stability, immunogenicity or other physical, chemical or biological characteristics of the biologically active compound.

The invention is illustrated in the following examples:

in which we describe a method by which the 2-bromo, 2-methyl propionic acid bromide can be converted in the first instance to a water-soluble and reactive analogue that can be subsequently used to modify biological entities in aqueous media in order to prepare initiators for ATRP. The aqueous-reactive initiator can be attached to the biological molecule and then the entire entity used to initiate ATRP in water, or alternatively, the reactive initiator itself can be used to grow a polymer chain with a reactive functionality, which can be subsequently reacted with the biological entity in a later reaction to form the polymer-modified molecule.

EXAMPLE 1a

Preparation of 4-(3-(2-bromo, 2-methyl-propionate) phenyl)-propionic acid N-hydroxysuccinimide ester To a solution of 4-(3-hydroxyphenyl)-propionic acid (a) in acetonitrile, TMEDA (0.55 equiv) is added and stirred at room temperature for about 5 min. A solution of 2-bromo, 2-methyl propionic acid bromide (b) (1.5 equivalent) in acetonitrile is slowly added. After about 15 min of addition a white precipitate should be observed in the reaction vessel. After addition of the acid bromide (about 30 min), the reaction was stirred for a further 60 min approximately. The reaction mixture is filtered and the solvent was removed in vacuo to yield 4-(3-(2-bromo, 2-methyl-propionic ester)phenyl)-propionic acid (c).

To a solution of 4-(3-(2-methyl-propionate)phenyl)-propionic acid (1 equivalent) in THF, N-hydroxy succinimde (1.05 equivalents) and dicyclohexylcarbodi-imide (d) (1.05 equivalents) is added at −18° C. and stirred for about 2 h. The reaction was allowed to warm to room temperature and stirred for a further 10 h approximately. The reaction is worked up as described by Rutinger & Ruegg in Biochem J., 133(3), 538, 1973 to yield 4-(3-(2-bromo, 2-methyl-propionate)phenyl)-propionic acid N-hydroxysuccinimide ester (e).

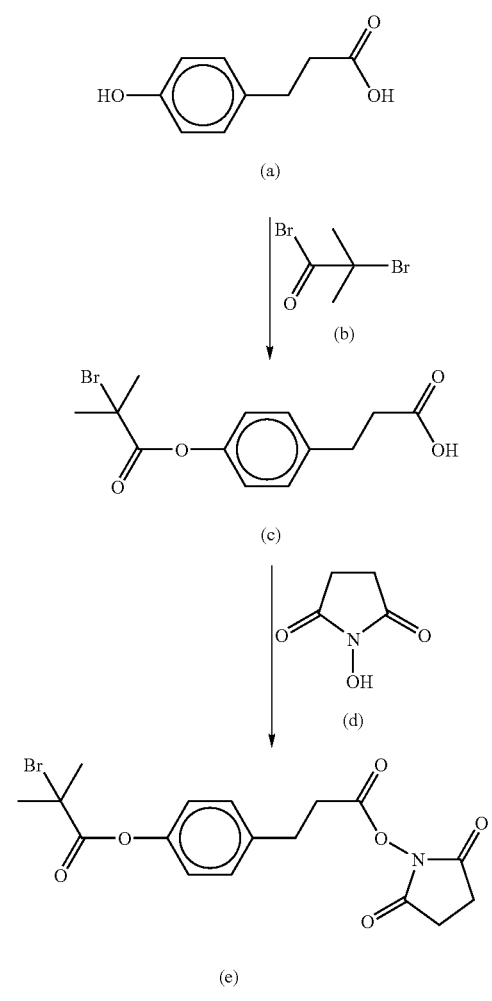

EXAMPLE 1b

Preparation of 2-bromo, 2-methyl-propionic acid N-hydroxysuccinimide ester

To a solution of 2-bromo, 2-methyl-propionic acid (a1) (1 equivalent) in THF, N-hydroxy succinimde (1.05 equivalents) and dicyclohexylcarbodi-imide (d) (1.05 equivalents) is added at −18° C. and stirred for about 2 h. The reaction is allowed to warm to room temperature and stirred for about a further 10 h. The reaction is worked up as described by Rutinger & Ruegg in Biochem J., 133(3), 538, 1973 to yield 2-bromo, 2-methyl-propionic acid N-hydroxysuccinimide ester (e1).

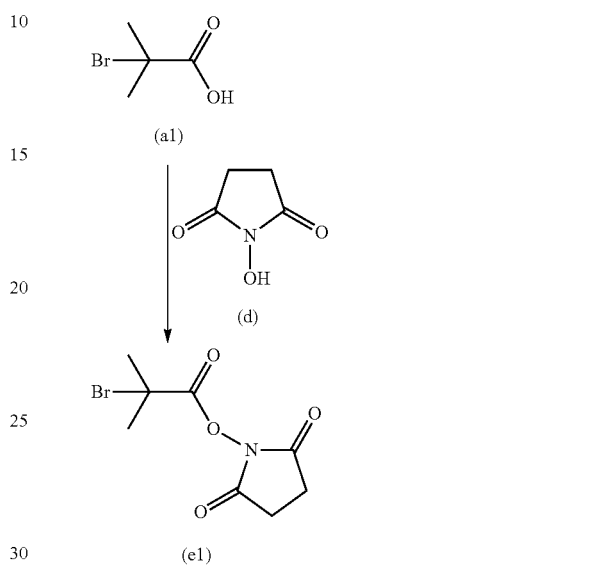

EXAMPLE 2

ATRP Using a Lysozyme-Modified Initiator a) To a suspension of 4-(3-(2-bromo, 2-methyl-propionate)phenyl)-propionic acid N-hydroxysuccinimide (e) ester in borate buffer, lysozyme is added and the resulting mixture gently shaken at room temperature for about 8 h. The initiator (f) was used without isolation.

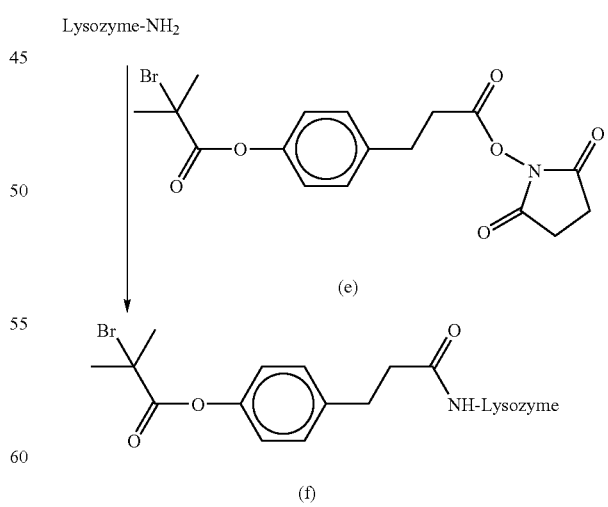

b) The initiator solution is purged with nitrogen for about 30 min, and then copper bromide catalyst and the bipyridyl ligand added. The solution is further purged with nitrogen, and MPC added (50× catalyst concentration, target Mn 15

000). The green reaction mixture was stirred for about 8 h at room temperature. The reaction is monitored by NMR aliquots, for consumption of the MPC methacrylate groups. The reaction mixture is analysed and product (g) purified by Capillary Electrophoresis. The conjugated lysozyme may be tested for its activity by a standard assay.

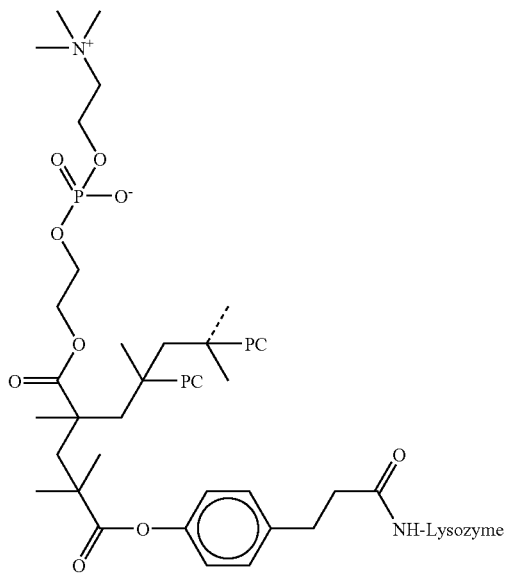

(g)

EXAMPLE 3

ATRP Using the 4-(3-(2-bromo-2-methyl-propionate)phenyl)-propionic acid N-hydroxysuccinimide ester a) The initiator solution (4-(3-(2-bromo-2-methyl-propionate)phenyl)-propionic acid N-hydroxysuccinimide ester (e) in methanol) is purged with nitrogen for about 30 min, and then copper bromide catalyst and the bipyridyl ligand added. The solution was further purged with nitrogen, and MPC added (50× catalyst concentration, target Mn 15 000). The green reaction mixture is stirred for about 8 h at room temperature. The reaction is monitored by NMR aliquots, for consumption of the MPC methacrylate groups. The reaction mixture is purified on a silica gel column to yield 4-(3-(2-poly-Pm, 2-methyl-propionate)phenyl)-propionic acid N-hydroxysuccinimide ester (h).

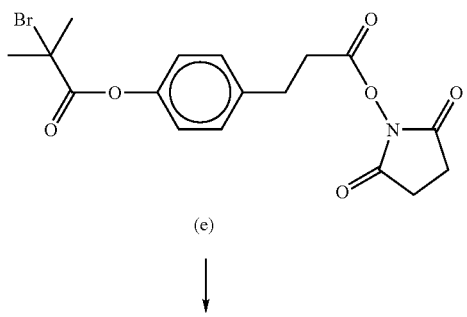

(e)

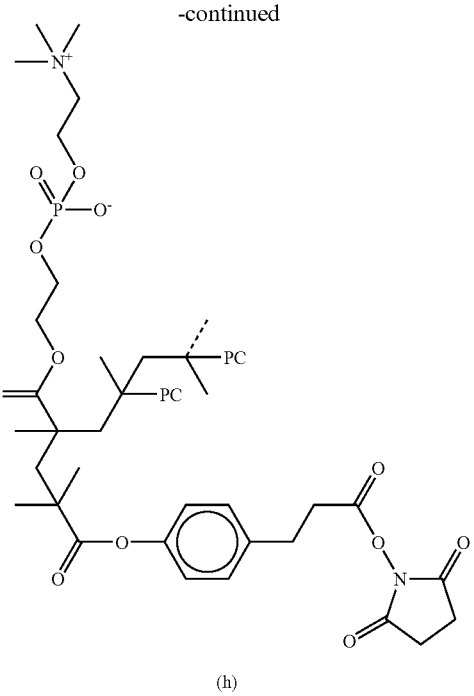

(h)

b) To a suspension of 4-(3-(2-poly-Pm, 2-methyl-propionate)phenyl)-propionic acid N-hydroxysuccinimide ester in borate buffer, lysozyme is added and the resulting mixture stirred at room temperature for about 12 h. The reaction mixture is again analysed and the product (g) purified by Capillary Electrophoresis. The activity of the conjugated lysozyme may be determined by a standard assay.

EXAMPLE 4

N-butyraldehyde 2-bromoisobutylamide

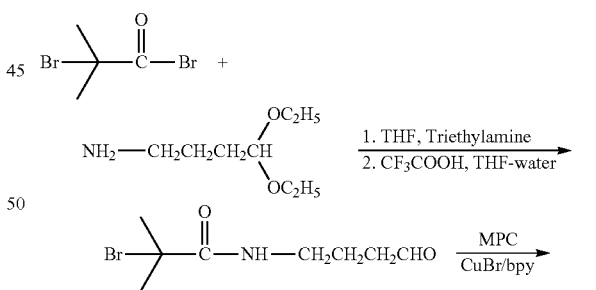

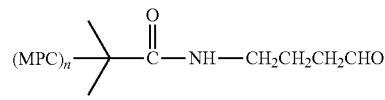

5 n = 50
6 n = 100

To 100 ml of dry THF, 8.1 g (0.05 mol) 4-aminobutyraldehyde diethyl acetal and 8.4 ml (0.06 mol) triethylamine were added. The reaction flask was kept in ice-water bath, and 2-bromoisobutyryl bromide (7.5 ml, 0.06 mol) was added dropwise by a syringe over 30 min. The reaction was then stirred for 2 hours at room temperature. The white amine halide salt precipitate was filtered off by Buchner funnel.

After evaporating half of the THF under reduced pressure, the filtered THF solution was treated with 25 ml of 20% trifluoroacetic acid aqueous solution overnight to cleave the diethyl acetal protection group. The mixture was neutralised by addition of 5% of $NaHCO_3$ water solution to pH 8, and the product aldehyde was extracted three times by 50 ml DCM each time. After evaporation of DCM, a red-yellow liquid was obtained. Further purification was carried out by silicon column using DCM as eluent. The final product is colorless liquid, and stored at −20° C. freezer.

The product may be conjugated to lysozyme by a reductive amination process in which a Schiff base is formed. This general technique is known for derivatising proteins having available primary amine groups.

The invention claimed is:

1. A process for forming a biologically active conjugate compound, comprising a conjugation step in which a biologically active starting material of the general formula I

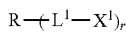

is reacted in an amide bond forming step with a reagent of the general formula II

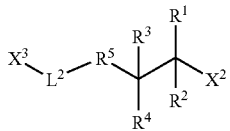

to form an amide-linked conjugate, the process increasing the stability of the biologically active starting material, in which R is a biologically active moiety;

$L^1$ is a bond or a divalent organic linker; and $X^1$ is —$NHR^6$ or —$COR^7$, in which $R^6$ is selected from the group consisting of hydrogen, $C_{1-6}$ alkyl, aryl and amine activating group and $R^7$ is hydroxyl or a carboxyl activating group;

$X^2$ is selected from the group consisting of a polymer formed from ethylenically unsaturated monomers and joined through a terminal group;

$R^1$ and $R^2$ are each independently selected from the group consisting of H, halogen, $C_1$-$C_{20}$ alkyl, $C_3$-$C_8$ cycloalkyl, $C(=O)R^{15}$, $C(=O)NR^{16}R^{17}$, COCl, OH, CN, $C_2$-$C_{20}$ alkenyl, oxiranyl, glycidyl, aryl, heterocyclyl, aralkyl and aralkenyl, in any of which the alkyl, alkenyl or aryl, heterocyclyl or cycloalkyl groups there may be from 1 to 3 substituents selected from the group consisting of hydrogen, hydroxy $C_1$-$C_4$ alkoxy, acyloxy, aryl, heterocyclyl, $C(=O)R^{15}$, $C(=O)NR^{16}R^{17}$, oxyranyl and glycidyl; $R^{15}$ is selected from the group consisting of alkyl of from 1 to 20 carbon atoms, alkoxy of from 1 to 20 carbon atoms, oligo(alkoxy) in which each alkoxy group has 1 to 3 carbon atoms, aryloxy and heterocyclyloxy, any of which groups may have substituents selected from the group consisting of optionally substituted alkoxy, oligoalkoxy, amino and hydroxyl groups;

$R^{16}$ and $R^{17}$ are independently selected from the group consisting of H and alkyl of from 1 to 20 carbon atoms which alkyl groups, may have substituents selected from the group consisting of alkoxy, acyl, acyloxy, alkoxycarbonyl, alkenoxycarbonyl, aryl and hydroxy, or $R^{16}$ and $R^{17}$ may be joined together to form an alkanediyl group of from 2 to 5 carbon atoms, thus forming a 3- to 6-membered ring;

$R^3$ and $R^4$ are independently selected from the group consisting of hydrogen, and $C_{1-6}$ alkyl, or $R^3$ and $R^4$ together are =O or =$NR^8$ where $R^8$ is hydrogen or $C_{1-4}$ alkyl;

$R^5$ is selected from the group consisting of a bond, —O—, —S— and divalent organic groups;

$L^2$ is a bond or a divalent linker and, where $X^1$ is $NHR^6$, $X^3$ is $COR^7$ and where $X^1$ is $COR^7$, $X^3$ is $NHR^6$ and r is an integer of at least 1, and wherein $X^2$ is a polymer chain consisting essentially of a homopolymer formed from 2-methacryloyloxyethyl-2'-trimethylammoniumethyl phosphate inner salt, and the compound of formula I is a protein, and wherein the compound of formula II is made in a preliminary polymerisation step in which ethylenically unsaturated monomers are polymerised in the presence of an initiator of the general formula XI

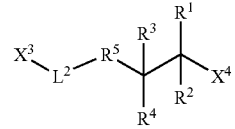

in which $X^3$, $L^2$ and $R^1$ to $R^5$ are as defined above and $X^4$ is selected from the group consisting of Cl, Br, I, $OR^{51}$, $SR^{52}$, $SeR^{52}$, $OP(=O)R^{52}$, $OP(=O)(OR^{52})_2$, O—N$(R^{52})_2$ and S—C(=S)N$(R^{52})_2$, where $R^{51}$ is alkyl of from 1 to 20 carbon atoms in which each of the hydrogen atoms may be independently replaced by halide, $R^{52}$ is aryl or a straight or branched $C_1$-$C_{20}$ alkyl group, and where an N$(R^{52})_2$ group is present, the two $R^{52}$ groups may be joined to form a 5- or 6-membered heterocyclic ring.

2. A process according to claim 1 in which the ethylenically unsaturated monomers are water-soluble.

3. A process according to claim 2 in which the polymerisation step is carried out in the presence of water.

4. A process according to claim 1 which is carried out in the presence of a catalyst which comprises a transition metal salt and a ligand.

5. A process according to claim 4 in which the ligand is bipyridine, or

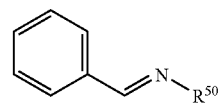

where $R^{50}$ is a suitable alkyl group triphenylphosphine or 1,1,4,7,10,10-hexamethyl-triethylene tetramine.

6. A process according to claim 4 in which the transition metal salt is copper (1) chloride, copper (1) bromide or ruthenium chloride.

* * * * *

UNITED STATES PATENT AND TRADEMARK OFFICE
CERTIFICATE OF CORRECTION

PATENT NO. : 8,053,520 B2  
APPLICATION NO. : 10/542333  
DATED : November 8, 2011  
INVENTOR(S) : Andrew Lennard Lewis et al.

Page 1 of 1

It is certified that error appears in the above-identified patent and that said Letters Patent is hereby corrected as shown below:

In the Specifications:

Column 5, line 8: change "$W^1N^{1-}R^{20}_3$" to -- $W^1N^+R^{20}_3$ --.

Column 6, line 46: change "—$N^{I-}(R^{36})_2(CH_2)_u COO^{I-}$" to -- —$N^+(R^{36})_2(CH_2)_u COO^-$ --.

Column 9, line 36: change "an" to -- a --.

Signed and Sealed this  
Twenty-fifth Day of June, 2013

Teresa Stanek Rea  
*Acting Director of the United States Patent and Trademark Office*